(12) United States Patent
Athanas et al.

(10) Patent No.: US 10,957,523 B2
(45) Date of Patent: Mar. 23, 2021

(54) 3D MASS SPECTROMETRY PREDICTIVE CLASSIFICATION

(71) Applicant: Thermo Finnigan LLC, San Jose, CA (US)

(72) Inventors: Michael J. Athanas, San Jose, CA (US); Hossein Arjomand, Cupertino, CA (US)

(73) Assignee: THERMO FINNIGAN LLC, San Jose, CA (US)

( * ) Notice: Subject to any disclaimer, the term of this patent is extended or adjusted under 35 U.S.C. 154(b) by 335 days.

(21) Appl. No.: 16/003,373

(22) Filed: Jun. 8, 2018

(65) Prior Publication Data
US 2019/0378702 A1 Dec. 12, 2019

(51) Int. Cl.
*G06F 11/00* (2006.01)
*H01J 49/00* (2006.01)
*G06K 9/62* (2006.01)

(52) U.S. Cl.
CPC .......... *H01J 49/0004* (2013.01); *G06K 9/628* (2013.01); *H01J 49/004* (2013.01); *H01J 49/0036* (2013.01)

(58) Field of Classification Search
CPC .................................................. H01J 49/0004
See application file for complete search history.

(56) References Cited

U.S. PATENT DOCUMENTS

| 7,899,625 | B2 | 3/2011 | Bhanot et al. | |
| 9,305,755 | B2* | 4/2016 | Yamaguchi | H01J 49/0036 |
| 9,547,821 | B1* | 1/2017 | Loreggia | G06N 3/08 |
| 2002/0193950 | A1 | 12/2002 | Gavin et al. | |
| 2004/0102906 | A1 | 5/2004 | Roder | |
| 2006/0245631 | A1* | 11/2006 | Levenson | G06K 9/6284 382/133 |
| 2007/0278395 | A1 | 12/2007 | Gorenstein et al. | |
| 2017/0271135 | A1 | 9/2017 | Yamaguchi | |

FOREIGN PATENT DOCUMENTS

| AU | 2002245043 B2 | 10/2006 |
| DE | 102010009853 A1 | 9/2011 |
| WO | 2013/039772 A1 | 3/2013 |
| WO | 2015/061597 A1 | 4/2015 |

(Continued)

OTHER PUBLICATIONS

America, et al., "Alignment and statistical difference analysis of complex peptide data sets generated by multidimensional LC-MS", Proteomics 2006, vol. 6 (2), pp. 641-653.

(Continued)

*Primary Examiner* — Phuong Huynh
(74) *Attorney, Agent, or Firm* — David A. Schell

(57) ABSTRACT

A method for analyzing a multidimensional data set includes generating a multidimensional mass spectrometry data set from a sample; and generating an matrix representing the multidimensional mass spectrometry data set such that a first dimension and a second dimension of the multidimensional mass spectrometry data set correspond to a matrix cell location, and an ion intensity corresponds to a matrix cell value; and determining a class of the matrix from a plurality of matrix classes using a trained neural network matrix classifier.

19 Claims, 7 Drawing Sheets

(56) References Cited

FOREIGN PATENT DOCUMENTS

WO 2017/153726 A1 9/2017

OTHER PUBLICATIONS

Hayasaka, et al.; "Development of imaging mass spectrometry (IMS) dataset extractor software, IMS convolution", Analytical and Bioanalytical Chemistry, Jul. 2011, vol. 401, Issue 1, pp. 183-193.
Skarysz et al., "Convolutional neural networks for automated targeted analysis of gas chromatography-mass spectrometry data", IN: 2018 International Joint Conference on Neural Networks (IJCNN), Rio de Janeiro, Brazil, Jul. 2018. https://dspace.lboro.ac.uk/2134/33052.

* cited by examiner

3D MASS SPECTROMETRY PREDICTIVE CLASSIFICATION

FIELD

The present disclosure generally relates to the field of multidimensional data analysis including 3D mass spectrometry predictive classification.

INTRODUCTION

Mass spectrometry can be used to perform detailed analyses on samples. Furthermore, mass spectrometry can provide both qualitative (is compound X present in the sample) and quantitative (how much of compound X is present in the sample) data for a large number of compounds in a sample. These capabilities have been used for a wide variety of analyses, such as to test for drug use, determine pesticide residues in food, monitor water quality, and the like.

When coupled with additional separation techniques, such as electrophoresis or chromatography, the mass spectrometry data can separate in new dimensions, including both a time dimension (retention time or elution time) and a mass-to-charge dimension. Additionally, MS/MS techniques can provide mass-to-charge information for both a precursor ion and fragments of the precursor ions.

However, multidimensional data sets can be complex. Traditionally, the raw data can be subjected to various routines for the extraction of specific information corresponding to specific components of the sample. However, the interdependence between components can lead to additional insights about the sample. As such, there is a need for improved data analysis techniques.

SUMMARY

In a first aspect, a system for analyzing a multidimensional data set can include a mass spectrometer, a matrix generator, and a matrix classifier. The mass spectrometer can be configured to generate a multidimensional data set from a sample; and provide the multidimensional data set to the matrix generator. The matrix generator can be configured to receive the multidimensional data set, generate a matrix representing the multidimensional data set such that a first dimension and a second dimension of the multidimensional data set correspond to a matrix cell location, and an ion intensity corresponds to a matrix cell value; and provide the image to an matrix classifier. The matrix classifier can be configured to receive the matrix from the matrix generator; and determine a class of the matrix from a plurality of matrix classes.

In various embodiments of the first aspect, (i) the matrix generator can be further configured to rescale the matrix prior to providing the matrix to matrix classifier or (ii) the matrix classifier can be further configured to rescale the matrix prior to determining the class of the matrix.

In various embodiments of the first aspect, determining the class of the matrix can be performed using a trained neural network.

In various embodiments of the first aspect, the first dimension can be retention time and the second dimension is mass-to-charge ratio.

In various embodiments of the first aspect, the multidimensional data set can be an MS/MS experiment, the first dimension can be precursor mass-to-charge ratio and the second dimension can be product mass-to-charge ratio.

In various embodiments of the first aspect, the matrix can be an image. In particular embodiments, the image can be a greyscale image with a single-color value per pixel. In particular embodiments, the image can be a color image with at least two color values per pixel, and additional dimensions correspond to the additional color values.

In a second aspect, a method for analyzing a multidimensional data set can include generating a multidimensional mass spectrometry data set from a sample; and generating an matrix representing the multidimensional mass spectrometry data set such that a first dimension and a second dimension of the multidimensional mass spectrometry data set correspond to a matrix cell location, and an ion intensity corresponds to a matrix cell value; and determining a class of the matrix from a plurality of matrix classes using a trained neural network matrix classifier.

In various embodiments of the second aspect, the method can further include rescaling the matrix prior to determining the class of the image.

In various embodiments of the second aspect, the first dimension can be retention time and the second dimension is mass-to-charge ratio.

In various embodiments of the second aspect, the multidimensional data set can be an MS/MS experiment, the first dimension can be precursor mass-to-charge ratio and the second dimension can be product mass-to-charge ratio.

In various embodiments of the second aspect, the matrix can be an image. In particular embodiments, the image can be a greyscale image with a single color value per pixel. In particular embodiments, wherein the image can be a color image with at least two color values per pixel, and additional dimensions correspond to the additional color values.

In a third aspect, a system for assessing an instrument can include the instrument, a matrix generator, and a matrix classifier. The instrument can be configured to perform a series of diagnostic routines; and provide results of the series of diagnostic routines to the matrix generator. The matrix generator can be configured to receive the results of the series of diagnostic routines; generate an multidimensional matrix representing the results of the series of diagnostic routines with a matrix cell location corresponding to one of the series of diagnostic routines and a time point during the diagnostic routine, and a value of the matrix cell corresponding to a measured value of the diagnostic routine; and provide the multidimensional matrix to the matrix classifier. The matrix classifier can be configured to receive the multidimensional matrix from the matrix generator; and determine a class of the multidimensional matrix from a plurality of matrix classes, the class indicating a corrective action necessary to bring the instrument into nominal operation.

In various embodiments of the third aspect, (i) the matrix generator can be further configured to rescale the multidimensional matrix prior to providing the multidimensional matrix to the matrix classifier or (ii) the matrix classifier can be configured to rescale the multidimensional matrix prior to determining the class of the multidimensional matrix.

In various embodiments of the third aspect, determining the class of the multidimensional matrix can be performed using a trained neural network.

In various embodiments of the third aspect, the multidimensional matrix can be an image. In particular embodiments, the image can be a greyscale image with a single color value per pixel. In particular embodiments, the image can be a color image with at least two color values per pixel, and additional dimensions corresponding to the system parameters can be monitored during the series of diagnostic routines.

In a fourth aspect, a method for analyzing a multidimensional data set can include performing a series of diagnostic routines on an instrument; generating an multidimensional matrix representing results of the series of diagnostic routines with a pixel location determined by the identity of a diagnostic routine of the series of diagnostic routines and a time point during the diagnostic routine, and a color value of the pixel corresponding to a measured value of the diagnostic routine; and determining a class of the multidimensional matrix from a plurality of matrix classes, the class indicating a corrective action necessary to bring the instrument into nominal operation.

In various embodiments of the fourth aspect, the method can further includes rescaling the multidimensional matrix prior to determining the class of the multidimensional matrix.

In various embodiments of the fourth aspect, determining the class of the multidimensional matrix can be performed using a trained neural network.

In various embodiments of the fourth aspect, the multidimensional matrix can be an image. In particular embodiments, the image can be a greyscale image with a single color value per pixel. In particular embodiments, the image can be a color image with at least two color values per pixel, and additional dimensions can correspond to the system parameters monitored during the series of diagnostic routines.

In a fifth aspect, a system for analyzing a multidimensional data set can include an image generator and an image classifier. The image generator can be configured to receive a multidimensional data set; generate an image representing the multidimensional data set such that a first dimension and a second dimension of the multidimensional data set correspond to a pixel location, and a third dimension corresponds to a color value, the third dimension being a detector intensity; rescale the image; and provide the rescaled image to an image classifier. The image classifier can be configured to receive the rescaled image from the image generator; and determine a class of the image from a plurality of image classes.

In various embodiments of the fifth aspect, determining the class of the image can be performed using a trained neural network.

In various embodiments of the fifth aspect, the first dimension can be related to time.

In various embodiments of the fifth aspect, the second dimension can be related to mass-to-charge ratio.

In various embodiments of the fifth aspect, the image can be a greyscale image with a single color value per pixel.

In various embodiments of the fifth aspect, the image can be a color image with at least two color values per pixel, and additional dimensions can correspond to the additional color values.

In a sixth aspect, a method of analyzing a multidimensional data set can include receiving a multidimensional data set; generating an image representing the multidimensional data set such that a first dimension and a second dimension of the multidimensional data set correspond to a pixel location, and a third dimension corresponds to a color value; rescaling the image; receiving the rescaled image from the image generator; and determining a class of the image from a plurality of image classes using a trained neural network image classifier.

In various embodiments of the sixth aspect, the first dimension can be related to time.

In various embodiments of the sixth aspect, the second dimension can be related to mass-to-charge ratio.

In various embodiments of the sixth aspect, the image can be a greyscale image with a single color value per pixel.

In various embodiments of the sixth aspect, the image can be a color image with at least two color values per pixel, and additional dimensions can correspond to the additional color values.

DRAWINGS

For a more complete understanding of the principles disclosed herein, and the advantages thereof, reference is now made to the following descriptions taken in conjunction with the accompanying drawings and exhibits, in which.

Figure 1:
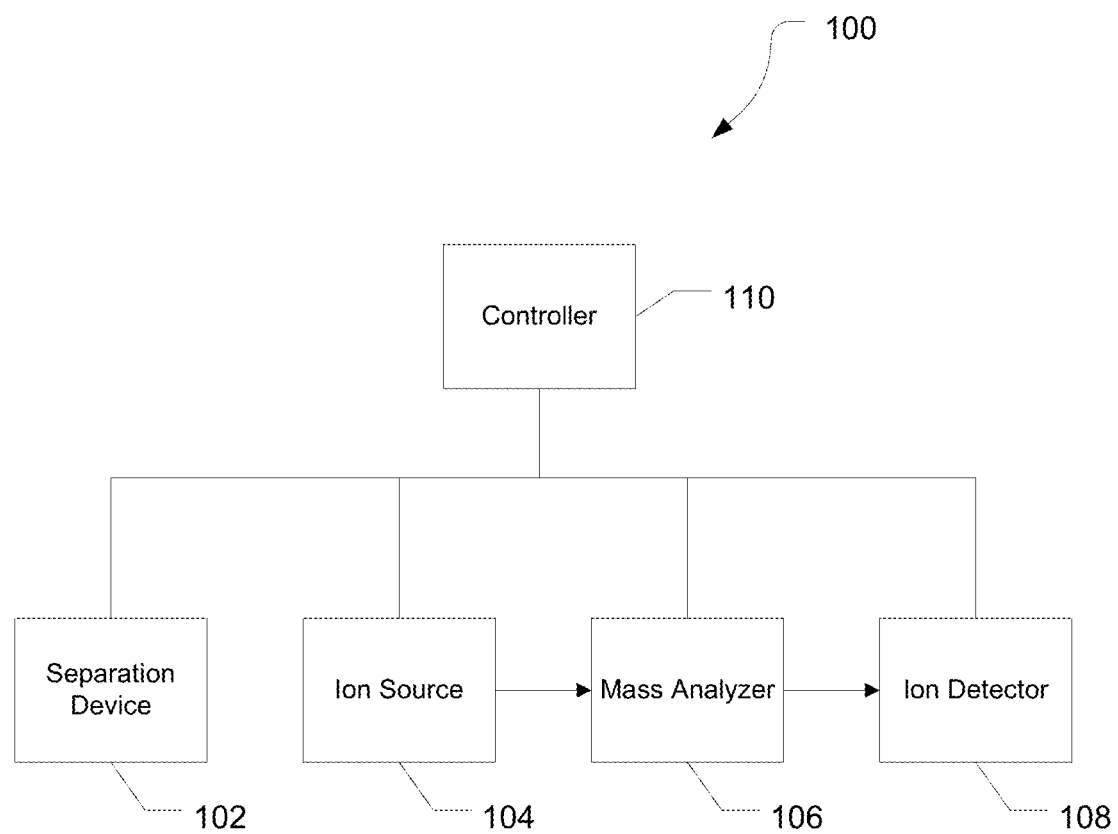
FIG. 1 is a block diagram of an exemplary mass spectrometry system, in accordance with various embodiments.

It is to be understood that the figures are not necessarily drawn to scale, nor are the objects in the figures necessarily drawn to scale in relationship to one another. The figures are depictions that are intended to bring clarity and understanding to various embodiments of apparatuses, systems, and methods disclosed herein. Wherever possible, the same reference numbers will be used throughout the drawings to refer to the same or like parts. Moreover, it should be appreciated that the drawings are not intended to limit the scope of the present teachings in any way.

DESCRIPTION OF VARIOUS EMBODIMENTS

Embodiments of systems and methods for ion isolation are described herein and in the accompanying exhibits.

The section headings used herein are for organizational purposes only and are not to be construed as limiting the described subject matter in any way.

In this detailed description of the various embodiments, for purposes of explanation, numerous specific details are set forth to provide a thorough understanding of the embodiments disclosed. One skilled in the art will appreciate, however, that these various embodiments may be practiced with or without these specific details. In other instances, structures and devices are shown in block diagram form. Furthermore, one skilled in the art can readily appreciate that the specific sequences in which methods are presented and performed are illustrative and it is contemplated that the sequences can be varied and still remain within the spirit and scope of the various embodiments disclosed herein.

All literature and similar materials cited in this application, including but not limited to, patents, patent applications, articles, books, treatises, and internet web pages are expressly incorporated by reference in their entirety for any purpose. Unless described otherwise, all technical and scientific terms used herein have a meaning as is commonly understood by one of ordinary skill in the art to which the various embodiments described herein belongs.

It will be appreciated that there is an implied "about" prior to the temperatures, concentrations, times, pressures, flow rates, cross-sectional areas, etc. discussed in the present teachings, such that slight and insubstantial deviations are within the scope of the present teachings. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the present teachings.

As used herein, "a" or "an" also may refer to "at least one" or "one or more." Also, the use of "or" is inclusive, such that the phrase "A or B" is true when "A" is true, "B" is true, or both "A" and "B" are true. Further, unless otherwise required by context, singular terms shall include pluralities and plural terms shall include the singular.

A "system" sets forth a set of components, real or abstract, comprising a whole where each component interacts with or is related to at least one other component within the whole.

Mass Spectrometry Platforms

Various embodiments of mass spectrometry platform 100 can include components as displayed in the block diagram of FIG. 1. In various embodiments, elements of FIG. 1 can be incorporated into mass spectrometry platform 100. According to various embodiments, mass spectrometer 100 can include an ion source 102, a mass analyzer 104, an ion detector 106, and a controller 108.

In various embodiments, the ion source 102 generates a plurality of ions from a sample. The ion source can include, but is not limited to, a matrix assisted laser desorption/ionization (MALDI) source, electrospray ionization (ESI) source, atmospheric pressure chemical ionization (APCI) source, atmospheric pressure photoionization source (APPI), inductively coupled plasma (ICP) source, electron ionization source, chemical ionization source, photoionization source, glow discharge ionization source, thermospray ionization source, and the like.

In various embodiments, the mass analyzer 104 can separate ions based on a mass to charge ratio of the ions. For example, the mass analyzer 104 can include a quadrupole mass filter analyzer, a quadrupole ion trap analyzer, a time-of-flight (TOF) analyzer, an electrostatic trap (e.g., ORBITRAP) mass analyzer, Fourier transform ion cyclotron resonance (FT-ICR) mass analyzer, and the like. In various embodiments, the mass analyzer 104 can also be configured to fragment the ions using collision induced dissociation (CID) electron transfer dissociation (ETD), electron capture dissociation (ECD), photo induced dissociation (PID), surface induced dissociation (SID), and the like, and further separate the fragmented ions based on the mass-to-charge ratio.

In various embodiments, the ion detector 106 can detect ions. For example, the ion detector 106 can include an electron multiplier, a Faraday cup, and the like. Ions leaving the mass analyzer can be detected by the ion detector. In various embodiments, the ion detector can be quantitative, such that an accurate count of the ions can be determined.

In various embodiments, the controller 108 can communicate with the ion source 102, the mass analyzer 104, and the ion detector 106. For example, the controller 108 can configure the ion source or enable/disable the ion source. Additionally, the controller 108 can configure the mass analyzer 104 to select a particular mass range to detect. Further, the controller 108 can adjust the sensitivity of the ion detector 106, such as by adjusting the gain. Additionally, the controller 108 can adjust the polarity of the ion detector 106 based on the polarity of the ions being detected. For example, the ion detector 106 can be configured to detect positive ions or be configured to detected negative ions.

Data Representation

Raw data generated by a chromatography-mass spectrometry system can comprise a collection of a large number of data points, with each data point having values for time (or other parameter, such as sequential scan number, which can be mapped to a time value), ion mass-to-charge ratio (m/z), intensity (relative or absolute), charge, resolution, estimation of signal quality, and signal baseline. In conventional data processing techniques, the raw data can be subjected to various routines for the extraction of information corresponding to specific ion species, with the ion species themselves corresponding to molecules in the sample (e.g., peptides or metabolites).

In various embodiments, the entire raw data set for an experimental run can be converted into a multidimensional dimensional matrix which, for example, can be mapped as an image, with time, m/z and intensity each representing one of the three orthogonal dimensions. Additional values, such as additional colors in an image, could take on other signal attributes mentioned above, such as charge and resolution. The resulting multidimensional matrix can then submitted to a pre-trained multidimensional matrix classifier tool, which can process the matrix to assign a category thereto.

Figure 2A:
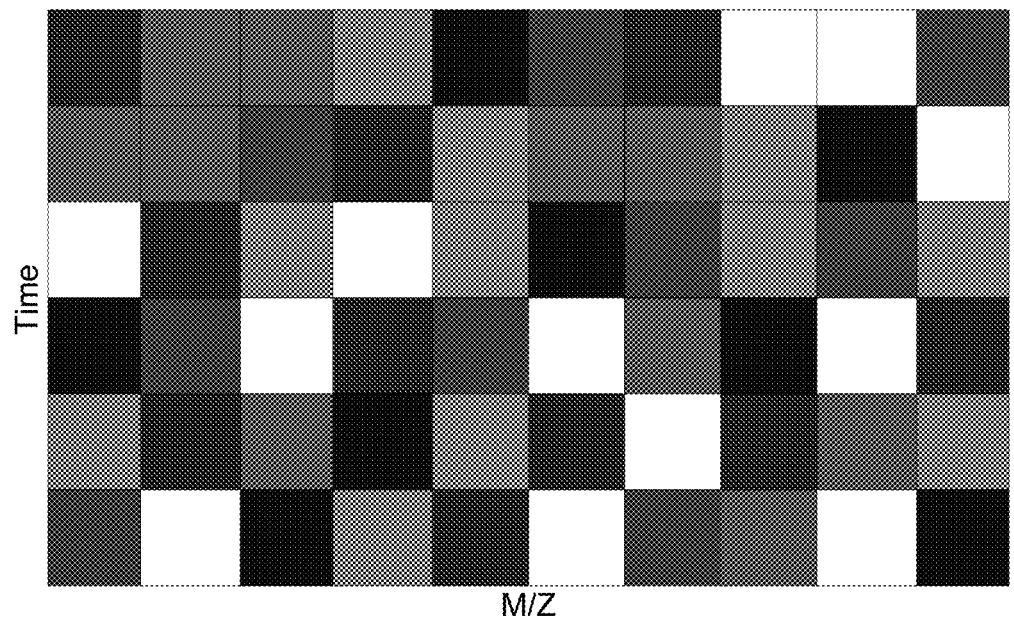
FIGS. 2A and 2B are diagrams illustrating multidimensional data sets represented in an image format, in accordance with various embodiments.
Figure 2B:
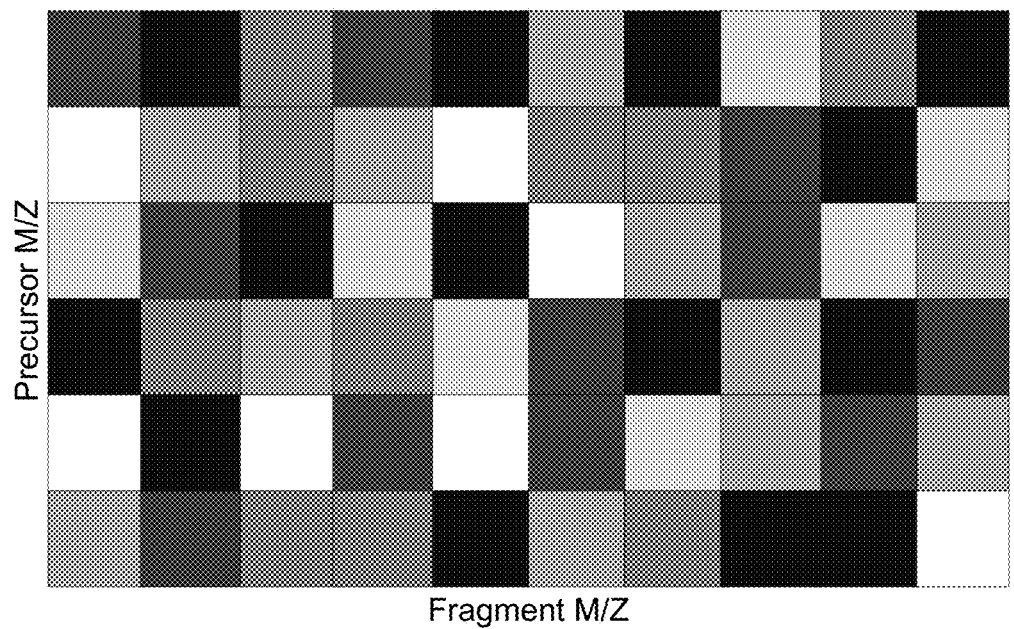

FIGS. 2A and 2B illustrate exemplary images that can be generated from mass spectrometry data. In FIG. 2A, the location of a pixel in X and Y correspond to the m/z and the time (such as retention time) while a pixel color intensity value can be derived from the signal intensity. FIG. 2B represents data from a MS/MS experiment, where the pixel location corresponds to the fragment and precursor m/z values while the pixel color intensity value can be derived from the signal intensity.

In various embodiments, the image can be a multi-color image (such as an RGB image) rather than a greyscale image. The intensity can be mapped to a first color value, such as red, while other measurements or values can be mapped to other color values. For example, charge state can be mapped to a second color value. In yet other embodiments, intensity values from different detectors can be mapped to different color values. For example, data from an ORBITRAP mass analyzer can be mapped to a first color value and data from a linear ion trap can be mapped to a second color value. In further embodiments, system diagnostics, such as pressure, temperature, or gas flow, or the like, can be mapped to various color values. In further embodiments, signal characteristics such as baseline, noise, offset, resolution, signal quality, low intensity range, high intensity range, and the like can be mapped to various color values. In yet further embodiments, color schemes with more than three color values can be used, such a CYMK encoding, to capture additional parameters. In yet further embodiments, any combination of the above encodings could be encoded into color values.

While chromatography-mass spectrometry data sets are used as an illustrative example, raw multidimensional data sets from a variety of sources can be converted to multidimensional image form for processing by a multidimensional matrix classifier. Many multidimensional data set can be mapped to an multidimensional matrix or image by mapping a first and second dimensions to the X and Y position and additional dimensions to one or more color values. In yet other embodiments, various system diagnostics or instrument health measures can be mapped to additional dimensions such as color values.

Figure 3:
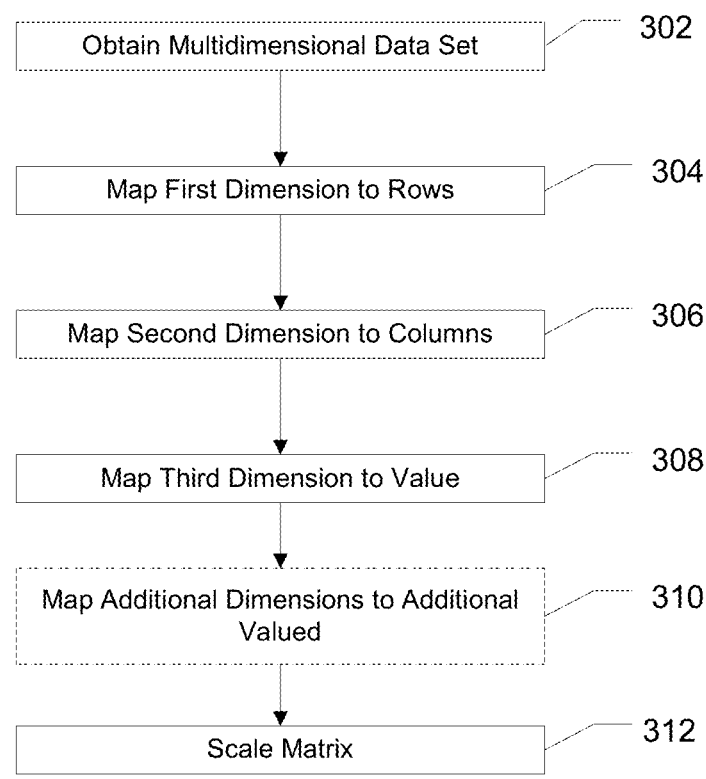
FIG. 3 is a flow diagram illustrating an exemplary method for generating an image file from a multidimensional data set, in accordance with various embodiments.

FIG. 3 illustrates a method of converting a raw multidimensional data set to an multidimensional matrix, such as an image. At 302, the multidimensional data set can be obtained. At 304, a first dimension (such as time) can be mapped to the pixel rows, and at 306, a second dimension (such as m/z) can be mapped to pixel columns. At 308, a third dimension can be mapped to a value, and, optionally, at 310, additional dimensions can be mapped to additional values. In various embodiments, the value dimension can be a list of values. For example, an RGB image representation includes three color values at each row and column (pixel) location.

At 312, the multidimensional matrix can be scaled to conform to the dimensions expected by a multidimensional matrix classifier. Generally, the multidimensional matrix classifier may be configured to receive an input matrix of a specific size but the multidimensional matrix may be larger or smaller than the input matrix size expected by the multidimensional matrix classifier. Additionally, the multidimensional matrix may be a different aspect ratio than expected by the multidimensional matrix classifier, so the multidimensional matrix may need to be scaled to a different aspect ratio. In various embodiments, the multidimensional matrix can be scaled by zero filling to achieve an expected number of rows and columns. Alternatively, various resampling and interpolation algorithms known in the art for image scaling, such as nearest neighbor interpolation, bilinear interpolation, bicubic interpolation, sinc resampling, lanczos resampling, box sampling, and the like, can be used to rescale the multidimensional matrix.

The image classifier tool may take the form of a commercially available machine learning-based multidimensional matrix classifier routine, such as Tensor Flow/Google Cloud Vision, Google Inception, Keras, MATLAB, IBM Watson, which has been pre-trained using raw data sets having known attributes. The classifier routine may employ known advanced techniques, such as convolutional neural networks, to improve the accuracy of the classification.

Figure 4:
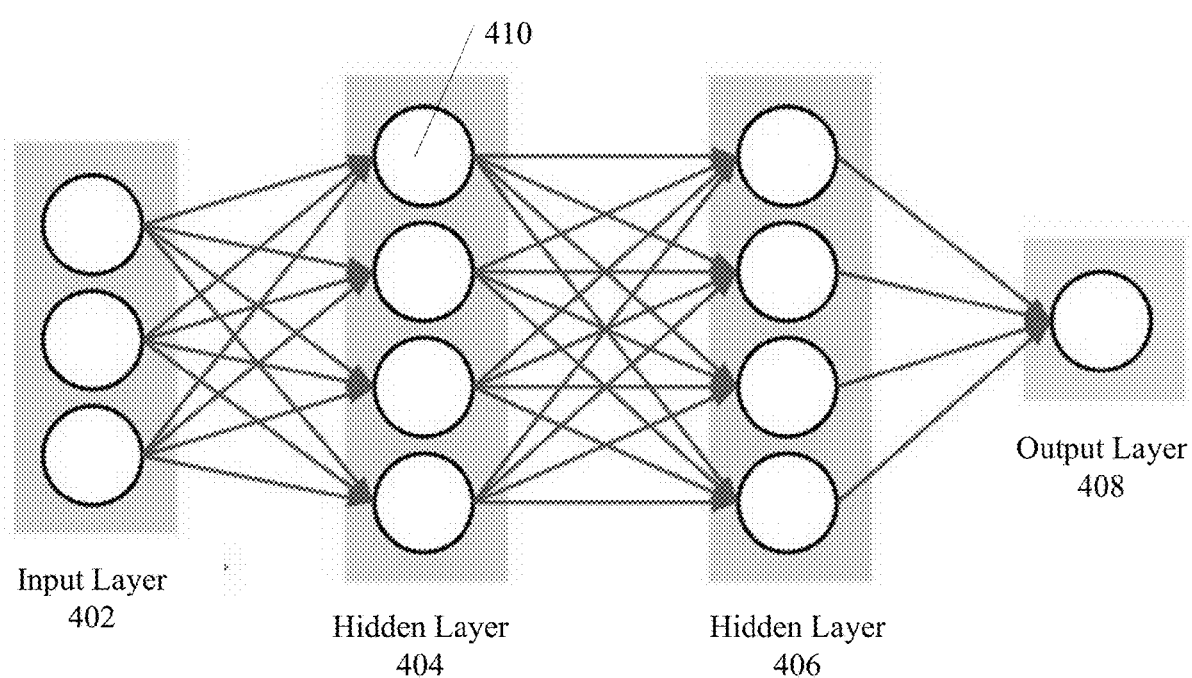
FIG. 4 is a diagram illustrating an exemplary deep learning network, in accordance with various embodiments.

FIG. 4 illustrates an exemplary matrix classifier. Matrix classifier 400 includes an input layer 402, hidden layers 404 and 406, and output layer 408. Each layer consists of a plurality of nodes 410, with each node having a weight. The input layer 402 can consist of the values in a data record that constitute inputs to the next layer 404 of nodes rather than full nodes. The nodes of a layer can be fully connected to the nodes of the next layer, such as, for example, each node 410 of input layer 402 can have a connection to each node 410 of hidden layer 404. The output layer 408 can include one node for each class. A single sweep forward through the network can result in the assignment of a value to each output node, and the record can be assigned to whichever class's node had the highest value. In various embodiments, when the highest and second highest output values are similar, the classification can be ambiguous. In another embodiment, where there is a simple binary classification, there can be a single output node, and the value of the node can determine the class. For example, a high value can be one classification, such as "yes", and a low value can the alternate classification, such as "no". In particular embodiments, an intermediate value can lead to an ambiguous classification, such as "maybe".

Figure 5:
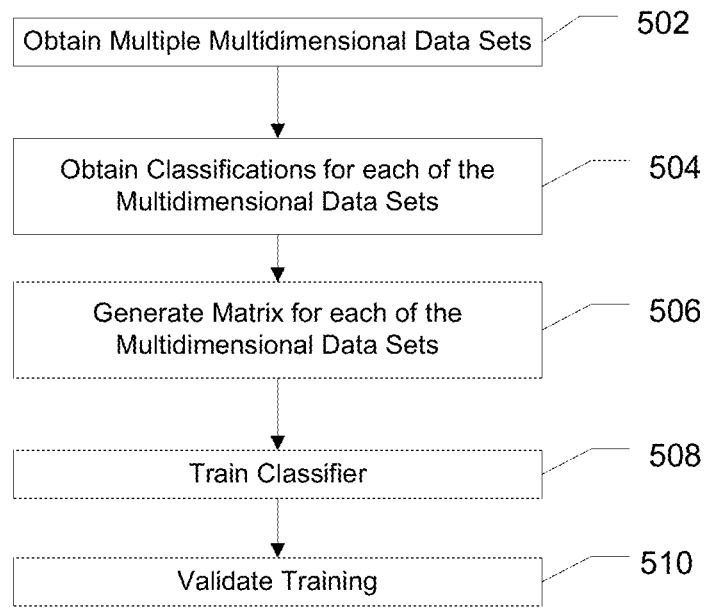
FIG. 5 is a flow diagram illustrating an exemplary method for training a deep learning network to classify multidimensional data sets, in accordance with various embodiments.

FIG. 5 is a flow diagram illustrating a method 500 of training a classifier. At 502, multiple multidimensional data sets are obtained, along with classifications for each of the data sets at 504. At 506, matrices corresponding to each of the data sets can be generated as previously discussed.

The classifier can be trained at 508. In various embodiments, initial weights for each node in the hidden layers can be assigned at random. The training matrices can be provided to the classifier one at a time. The resulting values of the output nodes can be compared to the correct classification for the matrix and the errors can be propagated backwards through the classifier to adjust the weighting of the nodes. The training matrices can be presented to the multiple times until the weights converge.

At 510, the training can be validated. In various embodiments, some number of the multiple data sets can be excluded from the training set. After training, the excluded matrices can be supplied to the classifier and the resulting classification determined by the classifier can be compared known classification for the corresponding data sets to verify that the classifier is producing the expected results.

Figure 6:
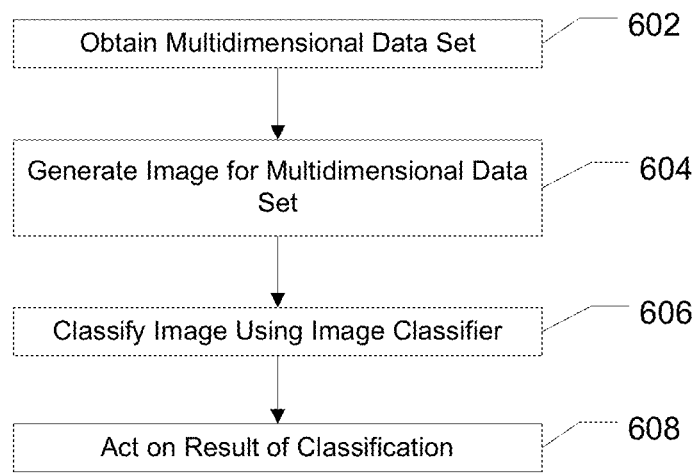
FIG. 6 is a flow diagram illustrating an exemplary method of using a deep learning network to classify a multidimensional data set, in accordance with various embodiments.

FIG. 6 illustrates an exemplary method 600 for using a multidimensional matrix classifier to classify a multidimensional data set. At 602, the multidimensional data set can be obtained, and, at 604, an image representing the data set can be generated. At 606, the matrix can be provided to the classifier and a classification for the matrix can be obtained.

At 608, an action can be taken based on the classification of the matrix.

In one particular example, each raw data set can represent an analysis of a biological tissue sample or extracts therefrom. The classifier tool can be configured to assign a category of diseased (e.g., cancerous), normal or indeterminate based on features in the 3D image constructed from. Provided that the training of the classifier is sufficiently robust, the classifier is tolerant of variability in the operation of the chromatography-mass spectrometry system used to acquire the data set, including chromatographic retention time shifts, and changes in sensitivity and mass accuracy. Based on the classification, further test can be ordered (indeterminate class) or a treatment plan can be started (diseased class).

In another particular example, each raw data set can represent the results of a multicomponent diagnostic or other measure of instrument health. The image classifier tool can be configured to assign various categories such as "normal behavior", "component X needs cleaning", or "component Y needs to be replaced". Based on the classification, the necessary action can be performed.

Computer-Implemented System

Figure 7:
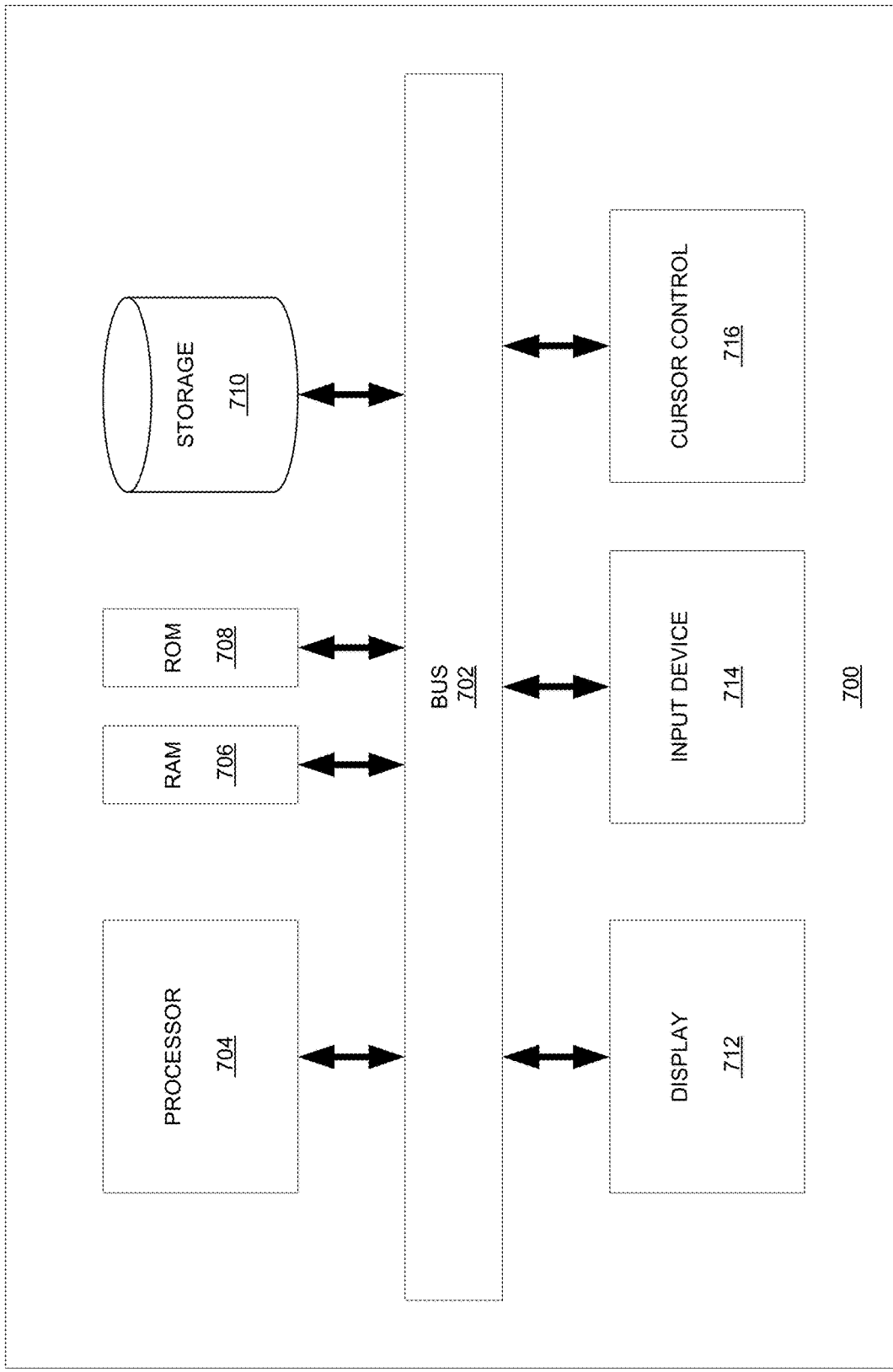
FIG. 7 is a block diagram illustrating an exemplary computer system.

FIG. 7 is a block diagram that illustrates a computer system 700, upon which embodiments of the present teachings may be implemented as which may incorporate or communicate with a system controller, for example controller 110 shown in FIG. 1, such that the operation of components of the associated mass spectrometer may be adjusted in accordance with calculations or determinations made by computer system 700. In various embodiments, computer system 700 can include a bus 702 or other communication mechanism for communicating information, and a processor 704 coupled with bus 702 for processing information. In various embodiments, computer system 700 can also include a memory 706, which can be a random access memory (RAM) or other dynamic storage device, coupled to bus 702, and instructions to be executed by processor 704. Memory 706 also can be used for storing temporary variables or other intermediate information during execution of instructions to be executed by processor 704. In various embodiments, computer system 700 can further include a read only memory (ROM) 708 or other static storage device coupled to bus 702 for storing static information and instructions for processor 704. A storage device 710, such as a magnetic disk or optical disk, can be provided and coupled to bus 702 for storing information and instructions.

In various embodiments, computer system 700 can be coupled via bus 702 to a display 712, such as a cathode ray tube (CRT) or liquid crystal display (LCD), for displaying information to a computer user. An input device 714, including alphanumeric and other keys, can be coupled to bus 702 for communicating information and command selections to processor 704. Another type of user input device is a cursor control 716, such as a mouse, a trackball or cursor direction keys for communicating direction information and command selections to processor 704 and for controlling cursor movement on display 712. This input device typically has two degrees of freedom in two axes, a first axis (i.e., x) and a second axis (i.e., y), that allows the device to specify positions in a plane.

A computer system 700 can perform the present teachings. Consistent with certain implementations of the present teachings, results can be provided by computer system 700 in response to processor 704 executing one or more sequences of one or more instructions contained in memory 706. Such instructions can be read into memory 706 from another computer-readable medium, such as storage device 710. Execution of the sequences of instructions contained in memory 706 can cause processor 704 to perform the processes described herein. In various embodiments, instructions in the memory can sequence the use of various combinations of logic gates available within the processor to perform the processes describe herein. Alternatively hard-wired circuitry can be used in place of or in combination with software instructions to implement the present teachings. In various embodiments, the hard-wired circuitry can include the necessary logic gates, operated in the necessary sequence to perform the processes described herein. Thus implementations of the present teachings are not limited to any specific combination of hardware circuitry and software.

Figure 8:
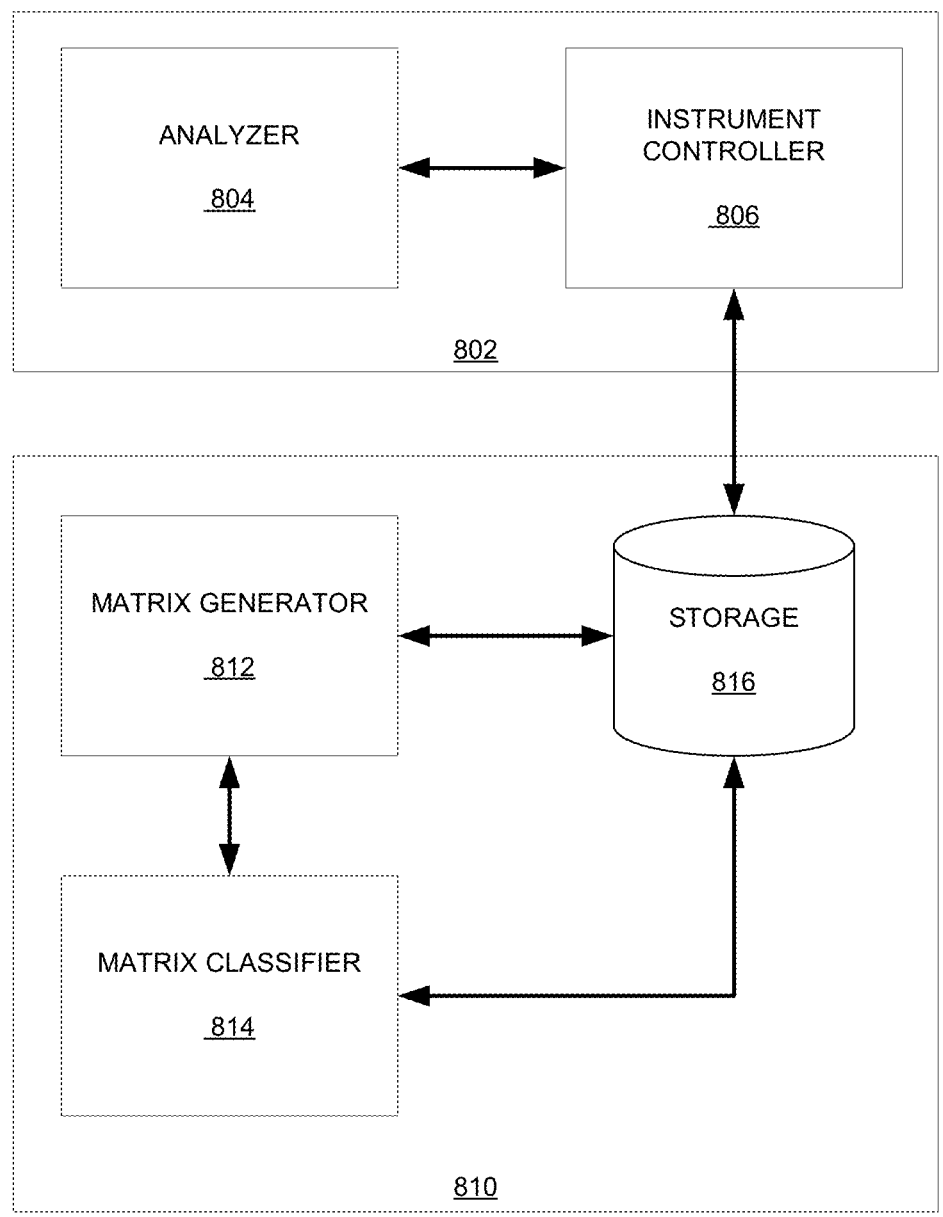
FIG. 8 is a block diagram illustrating an exemplary data analysis system, in accordance with various embodiments.

FIG. 8 is a block diagram that illustrates a data analysis system 800. In various embodiments, data processing system 800 can include a detection instrument 802 and a data processing system 810. The detection instrument 802 can include an analyzer 804 and an instrument controller 806. In various embodiments, the analyzer 804, under control of instrument controller 806, can take a sample and perform a series of actions to generate a data set, such as a multidimensional dataset. Instrument controller 806 can vary the operation of analyzer 804 in response to a preprogrammed series of actions, in response to data generated by analyzer 804, in response to instructions from data processing system 810, or any combination thereof. In other embodiments, instrument controller 806 can perform a series of diagnostic tests to verify the performance of analyzer 804, and the series of diagnostic tests can generate a multidimensional data set.

In various embodiments, the detection instrument 802 can correspond to mass spectrometry platform 100 shown in FIG. 1, with the analyzer 804 incorporating the ion source 102, the mass analyzer 104, and the ion detector 106 of FIG. 1, and instrument controller 806 corresponding to controller 108 of FIG. 1.

Data processing system 810 can include an image generator 812, an image classifier 814, and a storage 816. Image generator 812 can generate an image from the multidimensional data set and image classifier 814 can classify the image according to a preselected set of classifications. Storage 816 can store the multidimensional data set, the image, the classification of the image, or any combination thereof. In various embodiments, the image classification can indicate a required change to the operation of instrument 802, a determination of the data quality of the multidimensional dataset, a determination about the sample, a maintenance requirement for instrument 802, or the like.

The term "computer-readable medium" as used herein refers to any media that participates in providing instructions to processor 804 for execution. Such a medium can take many forms, including but not limited to, non-volatile media, volatile media, and transmission media. Examples of non-volatile media can include, but are not limited to, optical or magnetic disks, such as storage device 810. Examples of volatile media can include, but are not limited to, dynamic memory, such as memory 806. Examples of transmission media can include, but are not limited to, coaxial cables, copper wire, and fiber optics, including the wires that comprise bus 802.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, etc.

While the present teachings are described in conjunction with various embodiments, it is not intended that the present teachings be limited to such embodiments. On the contrary, the present teachings encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

What is claimed is:

1. A system for analyzing a multidimensional data set, comprising:
   a mass spectrometer configured to:
      generate a multidimensional data set from a sample; and
      provide the multidimensional data set to a matrix generator;
   the matrix generator configured to:
      receive the multidimensional data set;
      generate a matrix representing the multidimensional data set such that a first dimension and a second dimension of the multidimensional data set correspond to a matrix cell location, and an ion intensity corresponds to a matrix cell value; and
      provide the matrix to a matrix classifier; and
   the matrix classifier including a neural network trained using a supervised learning approach, the matrix classifier configured to:
      receive the matrix from the matrix generator; and
      using the neural network to determine a class of the matrix from a plurality of matrix classes.

2. The system of claim 1 wherein (i) the matrix generator is further configured to rescale the matrix prior to providing the matrix to matrix classifier or (ii) the matrix classifier is further configured to rescale the matrix prior to determining the class of the matrix.

3. The system of claim 1 wherein the first dimension is retention time and the second dimension is mass-to-charge ratio.

4. The system of claim 1 wherein the multidimensional data set is an MS/MS experiment, the first dimension is precursor mass-to-charge ratio and the second dimension is product mass-to-charge ratio.

5. The system of claim 1 wherein the matrix is an image.

6. The system of claim 5 wherein the image is a greyscale image with a single-color value per pixel.

7. The system of claim 5 wherein the image is a color image with at least two color values per pixel, and additional dimensions correspond to the additional color values.

8. A method for analyzing a multidimensional data set, comprising:
   generating a multidimensional mass spectrometry data set from a sample;
   generating an matrix representing the multidimensional mass spectrometry data set such that a first dimension and a second dimension of the multidimensional mass spectrometry data set correspond to a matrix cell location, and an ion intensity corresponds to a matrix cell value; and
   determining a class of the matrix from a plurality of matrix classes using a trained neural network matrix classifier, the trained neural network matrix classifier trained using supervised training with a training set of multidimensional mass spectrometry data sets and classifications of the multidimensional mass spectrometry data sets.

9. The method of claim 8 further comprising rescaling the matrix prior to determining the class of the image.

10. The method of claim 8 wherein the first dimension is retention time and the second dimension is mass-to-charge ratio.

11. The method of claim 8 wherein the multidimensional data set is an MS/MS experiment, the first dimension is precursor mass-to-charge ratio and the second dimension is product mass-to-charge ratio.

12. The method of claim 8 wherein the matrix is an image.

13. The method of claim 12 wherein the image is a greyscale image with a single color value per pixel.

14. The method of claim 12 wherein the image is a color image with at least two color values per pixel, and additional dimensions correspond to the additional color values.

15. A system for assessing an instrument, comprising:
   the instrument configured to:
      perform a series of diagnostic routines; and
      provide results of the series of diagnostic routines to a matrix generator;
   the matrix generator configured to:
      receive the results of the series of diagnostic routines;
      generate an multidimensional matrix representing the results of the series of diagnostic routines with a matrix cell location corresponding to one of the series of diagnostic routines and a time point during the diagnostic routine, and a value of the matrix cell corresponding to a measured value of the diagnostic routine; and
      provide the multidimensional matrix to a matrix classifier; and the matrix classifier including a neural network trained using supervised learning on a training set including multidimensional matrices and corresponding classifications, the matrix classifier configured to:
receive the multidimensional matrix from the matrix generator; and
using the trained neural network to determine a class of the multidimensional matrix from a plurality of matrix classes, the class indicating a corrective action necessary to bring the instrument into nominal operation.

16. The system of claim 15 wherein (i) the matrix generator is further configured to rescale the multidimensional matrix prior to providing the multidimensional matrix to the matrix classifier or (ii) the matrix classifier is configured to rescale the multidimensional matrix prior to determining the class of the multidimensional matrix.

17. The system of claim 15 wherein the multidimensional matrix is an image.

18. The system of claim 17 wherein the image is a greyscale image with a single color value per pixel.

19. The system of claim 17 wherein the image is a color image with at least two color values per pixel, and additional dimensions correspond to the system parameters monitored during the series of diagnostic routines.

* * * * *